United States Patent [19]

Kimura et al.

[11] Patent Number: 4,874,762
[45] Date of Patent: Oct. 17, 1989

[54] 2-AMINO-4-NICOTINOYLAMINO-6-ARYL-S-TRIAZINES AS NOOTROPIC AGENTS

[75] Inventors: Kiyoshi Kimura, Takatsuki; Fusao Ueda, Shiga; Masaru Tamura, Kyoto, all of Japan

[73] Assignee: Nippon Shinyaku Co., Ltd., Japan

[21] Appl. No.: 197,103

[22] Filed: May 20, 1988

[30] Foreign Application Priority Data

May 20, 1987 [JP] Japan .................. 62-124625

[51] Int. Cl.⁴ .............................. A61K 31/53
[52] U.S. Cl. .................................... 514/242
[58] Field of Search ......................... 514/242

[56] References Cited

U.S. PATENT DOCUMENTS 4,098,892  7/1978  Murai ................... 514/242

OTHER PUBLICATIONS

Chem. Abst. vol. 88-37844w (1978) 94-121615d (1981)+101-216409s (1984).

*Primary Examiner*—Stanley J. Friedman
*Attorney, Agent, or Firm*—Jacobs & Jacobs

[57] ABSTRACT

Compounds of the formula I

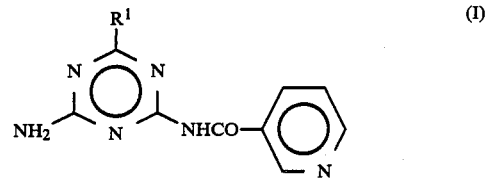

and pharmaceutically acceptable salts thereof wherein $R^1$ is hydrogen, lower alkyl, aryl or haloaryl, in combination with a pharmaceutically acceptable carrier.

9 Claims, No Drawings

2-AMINO-4-NICOTINOYLAMINO-6-ARYL-S-TRIAZINES AS NOOTROPIC AGENTS

The present invention is concerned with 2-amino-4-nicotinoylamino-6-substituted s-triazines as nootropic agents and pharmaceutically acceptable salts thereof which have been found to be useful as nootropic agents.

It is known in the art that such triazine derivatives have anti-ulcer activity (see Japanese publication No. 4751/80). It was surprising, therefore, when the present inventors, who had earlier discovered the anti-ulcer activity (see Japanese publication No. 4751/80), discovered the nootropic action since there is no known correlation between anti-ulcer activity and nootropic activity.

More particularly, therefore, the present invention is concerned with pharmaceutical compositions useful for its nootropic action in humans and animals which comprises a therapeutically effective amount of a compound of the formula I

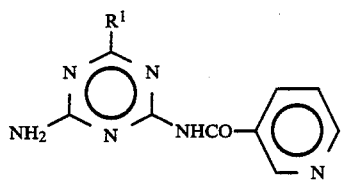

or a pharmaceutically acceptable salt thereof wherein $R^1$ is hydrogen, lower alkyl, aryl or haloaryl, in combination with a pharmaceutically acceptable carrier. Additionally, the present invention includes methods of treating dementia in humans and animals which comprises administering to a human or animal in need thereof a therapeutically effective amount of a compound of the formula I:

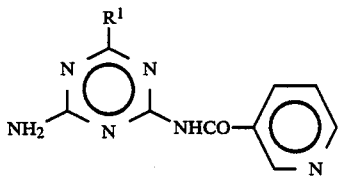

or a pharmaceutically acceptable salt thereof wherein $R^1$ is hydrogen, lower alkyl, aryl or haloaryl, in combination with a pharmaceutically acceptable carrier.

According to one embodiment of the present invention, the therapeutically effective amount of active agent in the pharmaceutical compositions is from about 0.01% to about 10%, preferably from about 0.1% to about 5% by weight.

According to another embodiment of the present invention, $R^1$ is hydrogen, alkyl of 1 to 6 carbon atoms, phenyl, naphthyl, or phenyl or naphthyl substituted by fluoro, chloro, bromo or iodo.

The following compounds are repsentative of those of the present invention (their melting points are given in degrees C.):

2-Amino-4-nicotinoylamino-6-phenyl-s-triazine, 240°–242° C.;

2-Amino-4-nicotinoylamino-6-(2,4-dichlorophenyl)-s-triazine, 239°–241° C.;

2-Amino-4-nicotinoylamino-6-(3,4-dichlorophenyl)-s-triazine, 276°–279° C.;

2-Amino-6-methyl-4-nicotinoylamino-s-triazine, 245°–247° C.;

2-Amino-4-nicotinoylamino-s-triazine, 240°–241° C.;

2-Amino-4-nicotinoylamino-6-(4-fluorophenyl)-s-triazine, 255°–260° C.;

2-Amino-4-nicotinoylamino-6-pentyl-s-triazine, 195°–196.5° C.;

2-Amino-4-nicotinoylamino-6-(2-chlorophenyl)-s-triazine, 224°–226° C.;

2-Amino-4-nicotinoylamino-6-(4-chlorophenyl)-s-triazine, 266°–268° C.;

2-Amino-4-nicotinoylamino-6-(3-chlorophenyl)-s-triazine, 260°–262° C.;

2-Amino-4-nicotinoylamino-6-(2-iodophenyl)-s-triazine, 125°–127° C.;

2-Amino-4-nicotinoylamino-6-(1-naphthyl)-s-triazine, 214°–216°;

2-Amino-4-nicotinoylamino-6-(2-naphthyl)-s-triazine, 242°–243°;

2-Amino-4-nicotinoylamino-6-(2-fluoro-3-naphthyl)-s-triazine, 230°–235° C.;

2-Amino-4-nicotinoylamino-6-(2-chloro-3-naphthyl)-s-triazine, 229°–230° C.; and

2-Amino-4-nicotinoylamino-6-(2-bromo-3-naphthyl)-s-triazine, 245°–247° C.

As the average age of the population increases, dementia becomes a more prevalent disease particularly for elderly people. Up to the present time, suitable therapeutic compounds have not yet been discovered which can be used on a widespread basis for the treatment of dementia. Present treatments include using drugs such as brain metabolism activators, brain circulation improving agents, tranquilizers, cholinergic agents, and the like. In addition, compounds including aniracetam and pramiracetam have been developed as nootropic agents. None of these, however, has proved satisfactory.

It, therefore, represents a significant breakthrough in dementia therapy to discover that the compounds of the formula I and pharmaceutically acceptable salts thereof as hereinbefore described are useful as nootropic agents.

The compounds of the present invention are per se known for other uses, i.e. anti-ulcer and can be manufactured according to methods per se known.

Activity against dementia has been confirmed by the following tests:

Improvement Effect on Amnesia Caused by Scopolamine

After rats acquired passive avoidance learning (i.e. acquisition trial), they were given 0.5 mg/kg scopolamine intraperitoneally and, immediately thereafter, they were given the drug test orally. After 1 hour, they were subjected to a passive avoidance test (retention trial) once again.

Positive reaction rates in each dose of the test drug (i.e. numbers of positive animals/used animals) are given in Table 1.

TABLE 1

| Test Drug (Compd. No.) | Positive Reaction Rates Doses (mg/kg) | | |
|---|---|---|---|
| | — | 1 | 3 | 10 |
| MC | ⅛ | | | |
| (5) | | 2/8 | 6/8* | |
| (6) | | | 5/8* | |

TABLE 1-continued

| Test Drug | Positive Reaction Rates Doses (mg/kg) | | | |
|---|---|---|---|---|
| (Compd. No.) | — | 1 | 3 | 10 |
| (7) |  |  | 5/8* |  |
| (16) |  |  | 5/8* |  |

*p < 0.05
MC stands for 0.5% methylcellulose solution

Thus the compounds of the present invention exhibited a significant improvement of amnesia at the doses of 3 mg/kg. It has been known that the toxicity of the present invention compounds is very low. For example, test compound 16 produced no death at all by oral administration of 1000 mg/kg.

When pharmaceutical compositions according to the present invention are prepared, suitable carriers include one or more liquid, solid or semisolid diluent, filler and other auxiliary agents for pharmaceutical preparations may be used. It is desired that the pharmaceutical compositions are administered in unit dosage form.

Oral administration can be effected utilizing solid and liquid dosage unit forms such as powders, tablets, capsules, granules and the like.

Powders are prepared by comminuting the compound to a suitable fine size and mixing with a similarly comminuted pharmaceutical carrier such as an edible carbohydrate as, for example, starch or mannitol. Flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated, for example, by preparing a powder mixture, granulating or slugging, adding a lubricant and disintegrant and pressing into tablets. A powder mixture is prepared by mixing the compound, suitably comminuted with a diluent or base as described above, and optionally, with a binder as carboxymethyl cellulose, an alginage, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds and pharmaceutically acceptable acid addition salts of the present invention can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous solution, while elixirs are prepared through the use of a nontoxic alcoholic vehicle. Suspensions can be formulated by dispersing the compound in a non-toxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a non-toxic liquid vehicle suitable for injection such as aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Non-toxic salts and salt solutions can be added to render the injection isotonic. Stabilizers, preservatives and emulsifiers can also be added.

Rectal administration can be effected utilizing suppositories in which the compound is admixed with low-melting, water-soluble or insoluble solids such as polyethylene glycol, cocoa butter, higher esters as for example flavored aqueous solution, while elixirs are prepared through myristyl palmitate or mixtures thereof.

While the therapeutically effective amount will vary with the past medical history of the patient, the age and condition and other factors which a physician normally takes into account including the root of adminitration, it is generally preferred to give from about 0.1 mg to about 30 mg of active agent per day to a human adult, preferably from about 1 mg to about 10 mg per day. However, it must be borne in mind that in some cases a lower dose may be sufficient, while in other cases, a higher dosage may be necessary or desirable. It is also desirable generally to administer the drug by dividing the total amount to be administered into one to three doses for administration.

The following nonlimitative examples more particularly illustrate the present invention:

EXAMPLE 1

Tablets were prepared by conventional manner from 4 mg of 2-amino-4-nicotinoylamino-s-triazine, 50 mg of lactose, 22 mg of corn starch, 5.1 mg of crystalline cellulose, 3.4 mg of hydroxypropylcellulose and 0.5 mg of magnesium stearate.

EXAMPLE 2

Fine granules were prepared by conventional manner from 4 mg of 2-amino-4-nicotinoylamino-s-triazine, 335 mg of lactose, 144.5 mg of corn starch, 1.5 mg of aqueous silicon dioxide and 15 mg of hydroxypropylcellulose.

We claim:
1. A method of treating dementia in humans and animals which comprises administering to a human or animal in need thereof a therapeutically effective amount of a compound of the formula I:

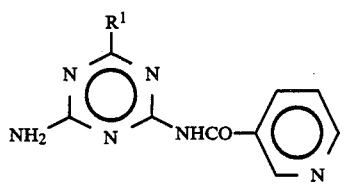

or a pharmaceutically acceptable salt thereof wherein $R^1$ is hydrogen, lower alkyl, aryl or haloaryl, in combination with a pharmaceutically acceptable carrier.

2. A method according to claim 1 wherein from about 0.1 mg to about 30 mg per day is administered to a human.

3. A method according to claim 1 wherein from about 1 mg to about 10 mg per day is administered to a human.

4. A method according to claim 1 wherein $R^1$ is hydrogen, alkyl of 1 to 6 carbon atoms, phenyl, naphthyl, or phenyl or naphthyl substituted by fluoro, chloro, bromo or iodo.

5. A method according to claim 1 wherein the compound is:
   2-Amino-4-nicotinoylamino-6-phenyl-s-triazine;
   2-Amino-4-nicotinoylamino-6-(2,4-dichlorophenyl)-s-triazine;
   2-Amino-4-nicotinoylamino-6-(3,4-dichlorophenyl)-s-triazine;
   2-Amino-6-methyl-4-nicotinoylamino-s-triazine;
   2-Amino-4-nicotinoylamino-s-triazine;
   2-Amino-4-nicotinoylamino-6-(4-fluorophenyl)-s-triazine;
   2-Amino-4-nicotinoylamino-6-pentyl-s-triazine;
   2-Amino-4-nicotinoylamino-6-(2-chlorophenyl)-s-triazine;
   2-Amino-4-nicotinoylamino-6-(4-chlorophenyl)-s-triazine;
   2-Amino-4-nicotinoylamino-6-(3-chlorophenyl)-s-triazine;
   2-Amino-4-nicotinoylamino-6-(2-iodophenyl)-s-triazine;
   2-Amino-4-nicotinoylamino-6-(1-naphthyl)-s-triazine;
   2-Amino-4-nicotinoylamino-6-(2-naphthyl)-s-triazine;
   2-Amino-4-nicotinoylamino-6-(2-fluoro-3-naphthyl)-s-triazine;
   2-Amino-4-nicotinoylamino-6-(2-chloro-3-naphthyl)-s-triazine; or
   2-Amino-4-nicotinoylamino-6-(2-bromo-3-naphthyl)-s-triazine.

6. A pharmaceutical composition in unit dosage form useful for its nootropic action in human wherein each dosage unit comprises from about 0.1 mg to about 30 mg of a compound of the formula I

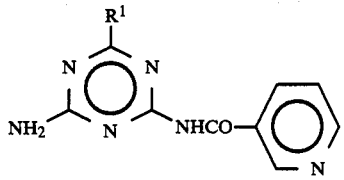

or a pharmaceutically acceptable salt thereof wherein $R^1$ is hydrogen, lower alkyl, aryl or haloaryl, in combination with a pharmaceutically acceptable carrier suitable for formulating dosage units for administration to humans.

7. A composition according to claim 1 wherein each dosage unit contains from about 1 mg to about 10 mg of the compound.

8. A composition according to claim 1 wherein $R^1$ is hydrogen, alkyl of 1 to 6 carbon atoms, phenyl, naphthyl, or phenyl or naphthyl substituted by fluoro, chloro, bromo or iodo.

9. A composition according to claim 1 wherein the compound is:
   2-Amino-4-nicotinoylamino-6-phenyl-s-triazine;
   2-Amino-4-nicotinoylamino-6-(2,4-dichlorophenyl)-s-triazine;
   2-Amino-4-nicotinoylamino-6-(3,4-dichlorophenyl)-s-triazine;
   2-Amino-6-methyl-4-nicotionylamino-s-triazine;
   2-Amino-4-nicotionylamino-s-triazine;
   2-Amino-4-nicotionylamino-6-(4-fluorophenyl)-s-triazine;
   2-Amino-4-nicotionylamino-6-pentyl-s-triazine;
   2-Amino-4-nicotinoylamino-6-(2-chlorophenyl)-s-triazine;
   2-Amino-4-nicotinoylamino-6-(4-chlorophenyl)-s-triazine;
   2-Amino-4-nicotinoylamino-6-(3-chlorophenyl)-s-triazine;
   2-Amino-4-nicotinoylamino-6-(2-iodophenyl)-s-triazine;
   2-Amino-4-nicotinoylamino-6-(1-naphthyl)-s-triazine;
   2-Amino-4-nicotinoylamino-6-(2-naphthyl)-s-triazine;
   2-Amino-4-nicotinoylamino-6-(2-fluoro-3-naphthyl)-s-triazine;
   2-Amino-4-nicotinoylamino-6-(2-chloro-3-naphthyl)-s-triazine; or
   2-Amino-4-nicotinoylamino-6-(2-bromo-3-naphthyl)-s-triazine.

* * * * *